United States Patent [19]

Pettrone et al.

[11] Patent Number: 5,240,835
[45] Date of Patent: Aug. 31, 1993

[54] METHODS FOR ENZYMATICALLY PREPARING POLYMERIZABLE MONOMERS

[75] Inventors: Frank A. Pettrone; Patrick J. Grisdale; Gregory M. Whited; Theresa C. Paulson, all of Rochester, N.Y.

[73] Assignee: Genencor International, Inc., South San Francisco, Calif.

[21] Appl. No.: 418,617

[22] Filed: Oct. 10, 1989

[51] Int. Cl.$^5$ .......................... C12P 7/62; C12P 19/04; C12N 9/10

[52] U.S. Cl. .................................... 435/91; 435/89; 435/101; 435/105; 435/135; 435/193; 435/843

[58] Field of Search ............... 435/105, 193, 843, 135

[56] References Cited

U.S. PATENT DOCUMENTS

| | | | |
|---|---|---|---|
| 3,558,431 | 1/1971 | Goodhue et al. | 195/49 |
| 3,823,070 | 7/1974 | Minato et al. | 195/28 R |
| 4,008,125 | 2/1977 | Kurozumi et al. | 195/51 R |
| 4,204,044 | 5/1980 | Suhara et al. | 435/280 |
| 4,415,657 | 11/1983 | Umezawa et al. | 435/106 |
| 4,594,324 | 6/1986 | Dalton et al. | 435/123 |

FOREIGN PATENT DOCUMENTS 280232  8/1988  European Pat. Off. ............ 435/135

OTHER PUBLICATIONS

Zaks et al., *Science*, 224, pp. 1249-1251 (1984).

*Primary Examiner*—Johnnie R. Brown
*Assistant Examiner*—Pamela S. Webber
*Attorney, Agent, or Firm*—Margaret A. Horn

[57] ABSTRACT

Unsaturated esters can be converted into unsaturated polymerizable monomers using a biocatalyst derived from *Corynebacterium oxydans*. The method involves the step of reacting an unsaturated ester with an organic compound having a primary or secondary hydroxy group in a substantially organic environment in the presence of the noted biocatalyst. A transacylase has been isolated from the microorganism and at least partially purified.

14 Claims, No Drawings

METHODS FOR ENZYMATICALLY PREPARING POLYMERIZABLE MONOMERS

FIELD OF THE INVENTION

This invention relates to a method of converting one organic compound into another using a biocatalyst. In particular, it relates to a method of converting unsaturated esters into unsaturated polymerizable monomers useful in preparing a variety of polymeric materials. It also relates to an at least partially purified transacylase isolated from *Corynebacterium oxydans* and a method of obtaining it.

BACKGROUND OF THE INVENTION

For decades now, synthetic polymers have been used in hundreds of products in all areas of human and animal life, ranging from industrial coatings to food additives to molded articles. Many of such polymers are technically defined as addition polymers generally prepared from polymerizable compounds known as ethylenically unsaturated polymerizable monomers. Upon reaction under standard polymerization conditions, the monomers are linked together in a long chain backbone in repeating units to form a high molecular weight compound.

Most polymers are prepared having certain properties which are provided by specific moieties or groups appended to the polymeric backbone. In some instances, such appended moieties are added to the backbone after polymerization using various known chemical reactions and reagents. This is often impossible or impractical, however, where the chemistry needed for appending the groups adversely affects the polymer itself or already appended groups in the polymer. Thus, polymer chemists and other researchers often try to find ways of appending desired groups to the polymerizable monomers prior to polymerization.

The preparation of ethylenically unsaturated polymerizable monomers is normally achieved using standard techniques such as those described by Rodriguez in his well known textbook entitled *Principles of Polymer Systems*, Hemisphere Publishing Co., 1982. That is, one or more vinyl moieties are introduced into the compound by the selective oxidation of isobutylene followed by esterification.

While such techniques have been generally successful in the past, there remain serious limitations on what types of groups can be appended to polymeric backbones either prior or subsequent to polymerization. The conditions of polymerization or monomer synthesis often adversely affect groups which one might want to append, such as thiols, groups with free hydroxyls or nucleotides. Thus, there is a continuing need for inexpensive, rapid and effective means for preparing polymerizable monomers which have a wide variety of potential appended groups.

The catalytic activity of enzymes is well known. It is also well known that certain microorganisms possess enzymes which can be used as biocatalysts outside of the host to prepare useful compounds from starting materials that act as substrates for the enzymes.

For example, biocatalysis is described for a porcine pancreatic lipase by Zaks et al (*Science*, 224, pp. 1249–1251, 1984). A strain belonging to the genus Corynebacterium is known to provide certain fatty acids from an n-paraffin according to U.S. Pat. No. 3,823,070. Alkenes are oxidized by a strain of *Methylococcus capsulatus* according to U.S. Pat. No. 4,594,324. Other biocatalytic reactions, including the production of optically active compounds, are described for example in U.S. Pat. Nos. 4,008,125 and 4,415,657.

EP-A-0 280 232 (published Aug. 9, 1988) describes and claims the use of a biocatalyst derived from *Corynebacterium oxydans* to make a monoacetate by reacting a diol with an ester of acetic acid. Moreover, U.S. Ser. No. 229,959 (filed Aug. 9, 1988 by Green, Goodhue and Olyslager) describes and claims the use of use of a biocatalyst derived from *Corynebacterium oxydans* to make a chiral hydroxycarboxylic acid from a prochiral diol.

While these two references describe important advances in the art of biocatalysis, they fail to show how to provide ethylenically unsaturated polymerizable monomers. Because there is considerable unpredictability in the preparation of such monomers, there is no certainty that the same procedures used for preparing saturated compounds can be used to make unsaturated ones. Conditions which favor desired reactions of saturated compounds often adversely affect unsaturated ones. In fact, in most chemical synthetic procedures, care must be taken to avoid saturating a double bond when preparing monomers.

There continues to be a need for an economical and simple way to make unsaturated polymerizable compounds which can have a wide variety of appended groups. It would be particularly desirable to avoid standard chemical synthetic methods and their attending problems, and to use biocatalysis.

SUMMARY OF THE INVENTION

The problems noted above are overcome and a significant advance in the arts of biocatalysis and polymer chemistry is provided by a method for the preparation of an unsaturated polymerizable monomer, the method comprising the step of reacting an unsaturated ester with an organic compound having a primary or secondary hydroxy group in a substantially organic environment in the presence of a catalytic amount of a biocatalyst derived from *Corynebacterium oxydans*.

The present invention provides a highly useful method for preparing unsaturated monomers which can have a wide variety of appended groups. Thus, the concerns encountered with traditional methods of making monomers are avoided. These advantages are achieved by using a biocatalyst derived from *Corynebacterium oxydans*.

In a preferred embodiment, the biocatalyst is an at least partially purified transacylase derived from *Corynebacterium oxydans*.

DETAILED DESCRIPTION OF THE INVENTION

The unsaturated compounds prepared using the method of the present invention are useful as intermediates in the synthesis of other compounds. More particularly, the prepared unsaturated compounds are unsaturated polymerizable compounds useful in the preparation of vinyl polymers. Most preferably, they are ethylenically unsaturated polymerizable monomers. Such polymers can have many uses as coatings, particles, molded articles, soft lenses, extruded polymers, ion-exchange resins and adhesives. More specific description of uses is provided below in relation to particular groups of monomers which can be prepared by this invention.

The biocatalyst used in the practice of this invention is derived from *Corynebacterium oxydans*. By "derived from" is meant that any composition that is made from this species of microorganism that catalyzes the reaction defined herein can be used. Useful compositions include a culture medium containing the cells, the recovered cells themselves, or extracts from the cells (such as an at least partially purified enzyme (which include the necessary catalytic activity. The method need not be carried out in the presence of viable cells as in a fermentation. The composition is used as the catalyst in the reaction.

The isolation, maintenance and characterization of a typical *Corynebacterium oxydans* is known in the art, such as the procedures described in U.S. Pat. No. 3,558,431. *Corynebacterium oxydans* is sometimes known in the art as *Flavobacterium oxydans*. Several strains of this microorganism are useful in the practice of this invention, namely ATCC No. 53586, ATCC No. 21245 and ATCC No. 53587 (American Type Culture Collection, Rockville, Md.). The strain identified as ATCC No. 53586 is preferred. The preparation of a useful composition of whole cells is described below as part of Example 1.

In a preferred embodiment, the biocatalyst is an at least partially purified transacylase derived from a strain of *Corynebacterium oxydans*, such as from the strains identified above. This enzyme extract is useful in the preparatory method of this invention, and particularly in the bioconversion reaction of the unsaturated esters described herein with the preferred diols, including but not limited to, 2,2-dimethyl-1,3-propanediol, ethylene glycol, 1-phenyl-1,3-propanediol, 1,3-propanediol, glycerol and glycidol. Specific cell growth and transacylase isolation and purification techniques are outlined in more detail in Example 1 below. In general, this procedure includes several steps which may include ammonium sulfate precipitation and protein separation techniques such as chromatography. At each stage of the purification, one can assay one or more fractions for transacylase activity. The transacylase can be used in completely purified state, or in a plurality purified state where there are some impurities present. Most preferably, there are only minor amounts of impurities present.

The transacylase can be further characterized as having a molecular weight of about 200,000 daltons.

A method for preparing an at least partially purified transacylase comprises the steps of:

A. lysing cells of *Corynebacterium oxydans* and separating water-insoluble cellular components from water-soluble cellular components, B. mixing a first extract of the water-soluble cellular components with ammonium sulfate and removing the precipitate formed thereby to form a second extract, C. subjecting the second extract to column chromatography on phenyl sepharose, D. pooling chromatographed fractions from step C determined to have transacylase activity to form a third extract, and subjecting the third extract to column chromatography on DEAE sepharose, E. pooling chromatographed fractions from step D determined to have transacylase activity to form a fourth extract, and mixing the fourth extract with ammonium sulfate to form a precipitate, F. resuspending the precipitate formed in step E in buffer and subjecting the resulting fifth extract to size exclusion chromatography, and G. collecting fractions obtained in step F which are determined to have transacylase activity.

Other strains of this species, not specifically identified herein, are believed to be useful as well. Any strain which will convert the unsaturated ester and hydroxy-containing organic compound into the unsaturated monomer as defined herein is useful in this invention. It would require only routine experimentation for a skilled worker in the art to determine if a particular strain was useful. Such experimentation would involve following the simple procedure outlined in Example 2 below and analyzing the products to identify them. If an unsaturated monomer is produced, the strain used in the reaction is a biocatalyst contemplated by this invention.

In the practice of this invention, the unsaturated esters useful include any acyl donor which has an unsaturated moiety on the carbonyl side of an oxycarbonyl group. The unsaturated moiety has at least one unsaturated group (that is, a double or triple unsaturated carbon-carbon bond), and preferably an ethylenically unsaturated group, which is conjugated with the carbonyl group. The esters also have a leaving group on the other side of the carbonyl group which includes the oxy linkage adjacent to the carbonyl. By "leaving group" is meant the nucleophile which is cleaves from the acyl donor upon substitution by another nucleophile which is incorporated into the unsaturated monomer.

More particularly, the useful unsaturated esters have the structure (I):

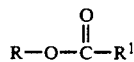

$$R-O-\overset{\overset{O}{\|}}{C}-R^1 \qquad \text{I}$$

wherein R is a saturated or unsaturated aliphatic, alicyclic or aromatic group which facilitates cleavage of R—O— from the rest of the molecule during the bioconversion reaction. Thus, R can be an substituted or unsubstituted alkyl of 12 to 18 carbon atoms (such as methyl, ethyl, propyl, isopropyl, t-butyl, hexyl and octadecyl), acyl, substituted or unsubstituted alkenyl or alkynyl of 2 to 18 carbon atoms (such as ethenyl, 1- or 2-propenyl, isopropenyl, ethynyl and 1-octadecenyl), substituted or unsubstituted cycloalkyl of 5 to 8 carbon atoms in the ring (such as cyclopentyl, cyclohexyl and cyclooctyl), cycloalkenyl of 5 to 8 carbon atoms in the ring (such as cyclopentenyl, cyclohexenyl and cyclooctenyl), substituted or unsubstituted aromatic having 6 to 10 carbon and heteroatoms in the ring (such as phenyl, tolyl, pyridyl, naphthyl, benzyl, and isoquinolinyl), substituted or unsubstituted nonaromatic heterocyclic of 5 to 8 carbon and heteratoms in the ring (such as pyrrollidinyl, tetrahydrofuryl and pipiridinyl, as well as any of the defined alkyl, alkenyl, cycloalkyl, cycloalkenyl, aromatic or nonaromatic heterocyclic groups linked together with one or more linkages, such as oxy, thio, amino, phosphono, carbonyl, oxycarbonyl, carbonimino and others known to one skilled in the art.

Preferably, R is an unsubstituted or substituted alkyl or alkenyl as defined above. Most preferred are substituted or unsubstituted alkyl groups having 1 to 3 carbon atoms and substituted or unsubstituted alkenyl groups having 2 or 3 carbon atoms in the backbone.

R' is alkenyl or alkynyl having 2 to 6 carbon atoms in the backbone. It can be unsubstituted or substituted with one or more alkyl groups having from 2 to 6 carbon atoms (such as methyl, ethyl, propyl, isopropyl, n-butyl and chloromethyl), halo (such as chloro or bromo), aryl of 6 to 10 carbon or heteroatoms (such as phenyl, xylyl and pyridyl) or cyano. The alkenyl or alkynyl must be conjugated with the carbonyl shown in structure I. Examples of useful unsaturated groups include vinyl, isopropenyl, allyl, styryl, cinnamyl, butadienyl 1-butenyl, 1-butynyl, 1-propenyl and 1-propynyl. Vinyl and isopropenyl are preferred.

Representative examples of unsaturated esters useful in the present invention include, but are not limited to, vinyl acrylate, vinyl methacrylate, methyl acrylate, ethyl acrylate, methyl methacrylate, ethyl methacrylate, itaconic acid, 1,2-hydroxyethyl dimethacrylate, 2H-pyran-2-one, methyl maleic acid, 2,4-hexadienedioic acid, 3,4,5-trihydroxy-1-cyclohexanecarboxylic acid and others which would be readily apparent to one skilled in the art. Methyl acrylate, ethyl acrylate, vinyl methacrylate and vinyl acrylate are preferred.

The hydroxy-containing organic compound useful in the practice of this invention can be any compound which has at least one primary or secondary (and preferably, primary) hydroxy group which will act as a nucleophile to undergo nucleophilic acyl substitution with the unsaturated ester defined above. Primary and secondary hydroxy groups have the art understood definition. Such compounds can be readily identified by putting a given compound in a reaction mixture with a diol in the presence of whole cells of *Corynebacterium oxydans* and observing after a sufficient period of time whether any unsaturated monomer is formed.

Particularly useful organic compounds are selected from the group consisting of polyols (having at least two hydroxy groups, one of which is a primary hydroxy group, such as ethylene glycol, neopentyl glycol, polyethylene glycol, 2,2-dialkyl-1,3-propane diols, 1,4-butanediol, 1,5-pentanediol, 2-propyl-1,3-propanediol, 1,3-propanediol and 2,2'-oxydiethanol), mono-, oligo- or polysaccharides (such as sucrose, glucose, sorbitol and D-glactal), glycerol or derivatives thereof (such as glycidol), mono- or oligonucleotides and cellulose or derivatives thereof.

More specifically, preferred primary alcohols are diols having the structure (II):

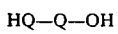

HQ—Q—OH  II wherein Q is a divalent aliphatic, alicyclic or aromatic moiety having a molecular weight of from about 60 to about 200.

The term aliphatic is defined as a saturated or unsaturated straight chain moiety made up of any number of carbon, hydrogen, nitrogen, oxygen, phosphorous or sulfur atoms in the backbone, and having any number of substituents chosen from alkyl groups of 1 to 18 carbon atoms, halo (such as chloro or bromo), alkoxy having from 1 to 18 carbon atoms or amino. Generally, the aliphatic group comprises one or more substituted or unsubstituted alkylene groups interrupted by heteroatoms (such as oxygen, sulfur, nitrogen or phosphorus). The term alicyclic refers to a nonaromatic, saturated or unsaturated cyclic group having from 5 to 8 carbon and heteroatoms, and includes carbocyclic moieties (such as cyclopentyldimethylene, cyclohexyldimethylene and others readily apparent to one skilled in the art) and heterocyclic moieties (such as tetrahydrofurfuryl, tetrahydropyrandimethylene and tetrahydrothiophenedimethylene). Divalent aromatic moieites include those having from 6 to 14 carbon and heteroatoms which posses aromaticity as that term is understood in the art. Useful aromatic moieties include phenyldimethylene, pyridyldimethylene, chloropyridyldimethylene, pyridoxinyl and thiophenedimethylene.

More preferably, Q is a linear or branched chain alkylene having from 4 to 20 carbon atoms, which alkylene can be unsubstituted or substituted (besides the alkyl groups in branches) with alkoxy of 1 to 18 carbon atoms, hydroxy, cyano, halo (such as chloro or bromo) or amino.

In some instances, the hydroxy-containing organic compounds is a prochiral or chiral diol or a racemic mixture thereof (such as 2-phenyl-1,3-propanediol and 2-isopropyl-1,3-propanediol). Prochiral diols can be converted into chiral diols by the bioconversion reaction of the present invention.

Representative primary alcohols useful in this invention include, but are not limited to, 2,2-dimethyl-1,3-propanediol, 1-phenyl-1,3-propanediol, glycidol, 1,4-butanediol, 1,5-pentanediol, 1,3-propandiol, 1,6-hexanediol, glycerol, ethylene glycol and 2-propyl-1,3-propanediol. Particularly useful diols include 2,2-dimethyl-1,3-propandiol, ethylene glycol, 1-phenyl-1,3-propandiol, 1,3-propandiol, glycerol and glycidol.

The primary alcohol can be chosen in the practice of this invention in order to provide useful polymerizable monomers for particular uses. For example, if Q in the structure (II) noted above is a prochiral moiety, the polymerizable monomer prepared by this invention can be used to form a prochiral polymer. As is known in the art, the term "prochiral" refers to a moiety which can be changed into a chiral moiety by changing a part of the moiety. There are many instances where polymers having prochiral or chiral moieties are useful, such as in aircraft coatings and chromatographic separations.

Of particular interest is the preparation of methacrylate polymers, for example poly(2-hydroxyethyl methacrylate) for soft optical lenses. Moreover, chiral polymers can be used as chiral stationary phases for liquid chromatographic separations.

In other instances, where Q is a mono-, oligo- or polysaccharide, the resulting monomer can be used to provide a polymer having appendant sucrose, sorbitol, glucose, galactal or mannitol. Such polymers are useful as food additives, sweeteners, fats or thixotropic agents.

Moreover, where Q represents an oligonucleotide, the resulting monomers can be used to prepare polymers having oligonucleotides attached thereto. Where a sufficient number of oligonucleotides are attached to polymeric surfaces, such as the surfaces of beads, the oligonucleotides can be used as capture probes in hybridization assays or other DNA assays where a nucleic acid (which may be amplified by polymerase chain reaction) is to be insolubilized for detection or separation from water-soluble materials. Nucleic acid separations could also be performed using such oligonucleotides attached to polymeric surfaces.

Other potential uses of polymers prepared from monomers resulting from the bioconversion method of this invention include such standard uses as films, coatings, molded articles, particulate materials, extruded polymers and others readily apparent to a polymer chemist.

The present method is carried out with a mixture of one or more unsaturated esters, one or more primary diols in the presence of the biocatalyst described above. The environment of the reaction mixture is substantially organic, meaning that less than about 10% (by volume) of water is present. The organic environment can be provided by the reactants themselves, or by nonreactive organic solvents, or both. Useful organic solvents include, but are not limited to, t-butylmethyl ether, tetrahydrofuran, diethyl ether and dichloromethane.

The reaction mixture can optionally contain small amounts of other materials. For example, a small amount of acid or base can be added to adjust the pH if necessary.

The molar ratio of the reactants in the reaction mixture can vary widely, and one skilled in the art can optimize the ratio for given reactants to obtain optimum yields with routine experimentation. Generally, the molar ratio of unsaturated ester to primary diol is from about 1:1 to about 120:1. A molar ratio of from about 50:1 to about 120:1 is preferred. The amount of biocatalyst is also widely variable with optimum amounts readily discoverable with minimal experimentation. Thus, a catalytic amount would vary depending upon the amounts of reactants, the conditions of reaction and the purity of the transacylase or concentration of whole cells. Generally, the biocatalyst is present in an amount of from about 0.5 to about 5% (by weight) for dry whole cells, with from about 1 to about 2% (by weight) being preferred. When at least partially purified transacylase is used, substantially less amounts are needed for acceptable bioconversion.

The reaction conditions are not critical. The temperature is generally in the range of from about 20° C. to about 50° C., with from about 25° C. to about 35° C. being preferred. The pH of the mixture (if any water is present) is generally from about 5 to about 9. Reaction times can vary depending upon the reactants and yields desired, with times between about 12 and about 72 hours being typical.

Preparation of Biocatalyst Composition

A biocatalytic composition containing whole cells useful in the practice of this invention can be prepared as follows. Cells of *C. oxydans* (ATCC 53586) were grown in common mineral salt medium (see for example, Stanier et al, *J. Cell Comp. Phys.*, 49, p. 25, 1957) containing yeast extract (0.05%, from Difco Laboratories) and succinic acid (1%). After 24–72 hours, the cells were harvested, washed with water, lyophilized and stored at 4° C. as a powder.

The following examples are presented for illustrative purposes. It is understood that other reactants and microbial strains could be used in preparing useful polymerizable monomers using similar procedures. Any needed modifications to the procedures for given reactants would be readily apparent to one skilled in the art in view of this teaching. All percentages of materials in this application are by weight unless otherwise indicated.

EXAMPLE 1

Isolation and Purification of Transacylase from *Corynebacterium Oxydans*

This example illustrates the procedure for isolating and at least partially purifying a transacylase from *Corynebacterium oxydans*. This transacylase has been found to be a biocatalyst in the practice of the method of this invention to prepare unsaturated polymerizable monomers (see Example 3 below).

Materials and Methods:

*C. oxydans* cells (ATCC 53586) were grown in a mineral salt medium containing yeast extract (0.05%) and structure (1%). The cells were harvested at late log phase, washed, lyophilized and stored at 4° C.

Standard chromatography media, phenyl sepharose, DEAE sepharose and S-300 sephacryl were obtained from Pharmacia Chemical Co.. DNase and bovine serum albumin were obtained from Sigma Chemical Co. Bicinchoninic acid protein assay reagents and N,O-bis(-trimethylsilyl)trifluoracetamide silylation reagent were purchased from Pierce Chemical Co. All other reagents and chemicals were obtained from Eastman Kodak Co. or other chemical companies in the highest purity available.

Protein determinations were performed using the Bicinchoninic Acid Protein reagent according to the manufacturer's instructions. Bovine serum albumin was used as the standard, the concentration of which was determined spectrophotometrically.

In the gas chromatography assay of the enzyme, cell extract (15 μl) was added to ethyl acetate (200 μl) containing 2,2-dimethyl-1,3-propanediol (108 mmolar) and the resulting mixture was incubated at 30°–37° C. with shaking for an appropriate time. The reaction was stopped by the addition of silylation reagent:pyridine (1:1) and heating at 60° C. for 20 minutes. Product formation was determined by capillary gas chromatography.

Column chromatography was carried out isothermally at 150° C. on a 25M AQ3-BP5, 1 μm column from Scientific Glass Engineering, Inc. The detection was accomplished using a standard flame ionization detection procedure. Since none of the substrate or product is metabolized during the reaction, the ratio of the substrate and product peaks can be used to calculate the product formed without a calibrated instrument or internal standard. Assays of column factions were done at different times and temperatures, as appropriate. Enzyme activity is expressed in Units/mg protein. One Unit is the amount of enzyme required to convert one μmole of substrate to product in one minute at 30° C.

In a p-nitrophenyl acetate method, appropriate amounts of cell extract were diluted to a final volume of 150 μl in potassium phosphate (50 mmolar, pH 7) and placed in wells of a standard 96 well microtiter plate. Reactions were initiated by the addition of potassium phosphate buffer (100 μl, 50 mmolar, pH 7) saturated with p-nitrophenyl acetate. The increase in absorbance at 410 nm was measured. Wells containing no protein were used to determine background.

Isolation of Cell Extract

All procedures were conducted at room temperature unless otherwise noted. A cell free extract was prepared by suspending cells (20 g) in potassium phosphate buffer (400 ml, 100 mmolar, pH 7) containing DNase (0.002%). The resulting mixture was sonicated on ice with stirring at 5 amp for 15 minutes (that is, 30 minutes pulsed at 50% of the duty cycle). The sonicated suspension was centrifuged at 25,000×g for 20 minutes. The resulting supernatant was a cell free extract of *C. oxydans*.

Purification of Transacylase

The cell free extract obtained above was centrifuged at 100,000×g for one hour and the supernatant was then used for further purification. Ammonium sulfate was added slowly over 30 minutes to a final concentration of 435 mmolar, and the precipitate formed was removed by centrifugation at 25,000×g for 20 minutes.

This extract was chromatographed on phenyl sepharose in the following manner: A phenyl sepharose column (500 mm in diameter and 70 mm in height) was equilibrated in potassium phosphate buffer (100 mmolar, pH 7.5) containing ammonium sulfate (425 mmolar). The column was pumped at 3 ml/min., 12 ml fractions were collected, and the absorbance with monitored at 280 nm. The supernatant from the cell free extract which had been centrifuged at 100,000×g (350 ml) containing ammonium sulfate (425 mmolar) was loaded on the column and unbound protein washed away with the above equilibrating buffer (240 ml). A 360 ml gradient from the equilibrating buffer to potassium phosphate buffer (10 mmolar, pH 6.5) was run followed by a 360 ml gradient to the same buffer containing ethanol (5%). Final conditions were maintained for 360 ml. Various fractions were assayed for transacylase activity using gas chromatography.

Fractions from the column chromatography containing enzyme activity (65-85) were pooled and the pH of the resulting extract was adjusted to 8.

This extract was then chromatographed on DEAE sepharose in the following manner: A DEAE sepharose column (50 mm in diameter and 70 mm in height) was equilibrated in tris(hydroxymethyl)aminomethane buffer (20 mmolar, pH 8). The column was pumped at 4 ml/min., 12 ml fractions were collected and the absorbance was monitored at 280 nm. Pooled fractions (240 ml) from the phenyl sepharose column, adjusted to pH 8, were loaded and the unbound protein was washed away with equilibrating buffer (120 ml). A 600 ml gradient to equilibrating buffer containing potassium chloride (500 mmolar) was run followed by maintaining final conditions for 480 ml. Various fractions were assayed for transacylase activity using gas chromatography.

Fractions containing transacylase activity (88-92) were pooled and the protein concentrated by precipitation with ammonium sulfate (70% saturation). The precipitated protein was collected by centrifugation and resuspended in potassium phosphate buffer (2 ml, 100 mmolar, pH 7).

This extract was separated by size exclusion chromatography in the following manner: A S-300 sephacryl column (26 mm in diameter by 900 mm in height) was equilibrated in potassium phosphate buffer (100 mmolar, pH 7). The column was pumped at 18 ml/hour, 4.5 ml fractions were collected and the absorbance with monitored at 280 nm. Active fractions, concentrated from DEAE chromatograph (2.0 ml), were loaded on the column and the protein eluted with equilibrating buffer. Certain fractions were assayed for transacylase activity using gas chromatography.

Fractions containing transacylase activity from the foregoing chromatography (62-66) were pooled. The following Table comprises a summary of the purification procedure and the transacylase activity of the various extracts.

TABLE

| Extract | Protein Volume (ml) | Protein mg/ml | Protein Total (mg) | Transacylase Activity Units/ml | Transacylase Activity Total Units | Specific Activity (Units/mg Protein) | % of Total | % of Previous Step | Purification Fold* |
|---|---|---|---|---|---|---|---|---|---|
| Cell free extract | 376 | 10.3 | 3873 | 2.09 | 823 | 0.20 | 100 | — | 1 |
| Centrifuged supernatant | 356 | 9.81 | 3492 | 2.01 | 762 | 0.21 | 93 | 93 | 1.1 |
| Fractions from Phenyl Sepharose Chromatography | 245 | 1.23 | 301 | 2.10 | 537 | 1.72 | 65 | 70 | 0.9 |
| Fractions from DEAE Sepharose Chromatography | 48 | 0.87 | 41.8 | 5.83 | 280 | 6.69 | 34 | 52 | 33.5 |
| Fractions from S-300 Size Exclusion Chromatography | 21.4 | 0.64 | 13.7 | 7.34 | 157 | 11.5 | 19 | 56 | 57.5 |

*This is a common term describing the ratio of specific activities.

EXAMPLE 2

Preparation of An Acrylate by Bioconversion Using Whole Cells

This example illustrates the practice of this invention to provide an ethylenically unsaturated polymerizable monomer using whole cells of *Corynebacterium oxydans*.

A solution of 2,2-dimethyl-1,3-propandiol (0.1 g) in ethyl acrylate (10 ml) was placed in a flask. This represents a 96:1 molar ratio of unsaturated ester to diol. Whole cells (0.1 g) of *Corynebacterium oxydans* and water (700 μl) were added to the flask, which was then stoppered and shaken at 30° C. and 300 rpm for 72 hours. The resulting monomer, 2,2-dimethyl-3-hydroxypropyl-1-propenoate, was formed in 21% yield (based on theoretical). The structure of the resulting monomer was confirmed using gas chromatography and mass spectral analysis.

EXAMPLE 3

Bioconversion Using Partially Purified Transacylase Derived from *Corynebacterium Oxydans*

This example illustrates the practice of this invention to prepare an ethylenically unsaturated polymerizable monomer using the partially purified transacylase obtained according to Example 1 above.

A solution (916 μl) containing 2,2-dimethyl-1,3-propandiol (20 mg) in vinyl acrylate (2 ml) was mixed, in a small vial, with an enzyme solution (64 μl) prepared according to Example 1 containing 7.34 I.U. of enzyme per ml of potassium phosphate buffer (100 mmolar, pH 7). This represents a molar ratio of unsaturated ester to primary alcohol of about 100:1. The vial was then stoppered and shaken at 30° C. and 300 rpm for 24 hours. The resulting ethylenically unsaturated polymerizable monomer, 2,2-dimethyl-3-hydroxypropyl-1-propenoate, was formed in 98.2% yield (based on theoretical). The structure of the resulting monomer was confirmed using gas chromatography and mass spectrometry.

The invention has been described in detail with particular reference to preferred embodiments thereof, but it will be understood that variations and modifications can be effected within the spirit and scope of the invention.

We claim:

1. A method for the enzymatic preparation of an unsaturated polymerizable monomer, said method comprising reacting:

a) an unsaturated ester of the formula:

$$R-O-\underset{\underset{O}{\|}}{C}-R' \quad (I)$$

wherein:

R is alkyl of 1-3 carbon atoms optionally substituted; and

R' is alkenyl or alkynyl having 2-6 carbon atoms; and b) an organic compound having a primary or secondary hydroxy group; in a ratio of said unsaturated ester to said organic compound having a primary or secondary hydroxy group of from about 1:1 to about 120:1, said reaction being carried out in an organic environment comprising less than about 10% (by volume) water, in the presence of from about 0.5% to about 5% (by weight) of a biocatalyst derived from *Corynebacterium oxydans*.

2. A method of claim 1 wherein said unsaturated ester is selected from the group consisting of vinyl methacrylate, methyl acrylate, ethyl acrylate and vinyl acrylate.

3. A method of claim 1 wherein said hydroxy-containing organic compound has at least one primary hydroxy group.

4. A method of claim 3 wherein said hydroxy-containing organic compound is selected from the group consisting of polyols, monosaccharides, oligosaccharides, polysaccharides, glycerols, mononucleotides, oligonucleotides and cellulose or derivatives thereof.

5. A method of claim 3 wherein said hydroxy-containing organic compound is a diol of the formula:

$$HO-Q-OH \quad (II)$$

wherein Q is selected from the group consisting of a divalent aliphatic, alicyclic or aromatic moiety having molecular weight of from about 60 to about 200.

6. A method of claim 5 wherein Q is selected from the group consisting of a linear or branched chain alkylene having 4-20 carbon atoms, which alkylene is optionally substituted with a substituent selected from the group consisting of alkoxy of 1 to 18 carbon atoms, hydroxy, cyano, halo or amino.

7. A method of claim 3 wherein said hydroxy-containing organic compound is a prochiral or chiral diol or a racemic mixture thereof.

8. A method of claim 1 wherein said biocatalyst is provided in whole cells of *Corynebacterium oxydans*.

9. A method for the preparation of an ethylenically unsaturated polymerizable monomer, said method comprising reacting:

a) acrylate or methacrylate; and b) a diol of the formula:

$$HO-Q-OH \quad (II)$$

wherein:

Q is selected from the group consisting of a divalent aliphatic, alicyclic or aromatic moiety having a molecular weight of from about 60 to about 200 in a molar ratio of said acrylate or methacrylate to said diol from about 50:1 to about 120:1, said reaction being carried out in an organic environment comprising less than 10% (by volume) water, in the presence of from about 0.5% to about 5% (by weight) of a biocatalyst derived from *Corynebacterium oxydans*.

10. A method of claim 9 wherein Q is a linear or branched chain alkylene having 4 to 20 carbon atoms.

11. A method of claim 9 wherein said diol is selected from the group consisting of: 2,2-dimethyl-1,3-propanediol, ethylene glycol, 1-phenyl-1,3-propanediol, 1,1-propanediol, glycerol, glycidol, 1,3-propanediol, 2-allyl-1,3-propanediol and D-galactol.

12. A method of claim 11 wherein said diol is 2,2-dimethyl-1,3-propanediol.

13. A method of claim 10 where said diol is a prochiral or chiral diol or a racemic mixture thereof.

14. A method of claim 9 wherein said ester is selected from the group consisting of vinyl acrylate, vinyl methacrylate, methyl acrylate and ethyl acrylate.

* * * * *